(12) United States Patent
Szwergold

(10) Patent No.: US 8,138,227 B2
(45) Date of Patent: Mar. 20, 2012

(54) METHOD FOR INHIBITING OR REVERSING NON-ENZYMATIC GLYCATION

(75) Inventor: Benjamin Szwergold, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/756,689

(22) Filed: Jun. 1, 2007

(65) Prior Publication Data

US 2008/0009547 A1    Jan. 10, 2008

Related U.S. Application Data

(60) Provisional application No. 60/806,661, filed on Jul. 6, 2006.

(51) Int. Cl.
*A61K 31/13* (2006.01)
(52) U.S. Cl. .......................... 514/665; 514/866
(58) Field of Classification Search .................. 514/562, 514/561, 564, 665, 866
See application file for complete search history.

(56) References Cited

U.S. PATENT DOCUMENTS

| | | | | |
|---|---|---|---|---|
| 4,794,124 | A | * | 12/1988 | Yamamoto et al. ............ 514/562 |
| 5,231,031 | A | * | 7/1993 | Szwergold et al. ............. 436/63 |
| 5,334,617 | A | | 8/1994 | Ulrich et al. |
| 5,688,828 | A | * | 11/1997 | Hellberg et al. ............... 514/565 |
| 6,004,958 | A | * | 12/1999 | Brown et al. ............... 514/238.8 |
| 6,498,193 | B2 | * | 12/2002 | Beisswenger et al. ........ 514/635 |
| 6,531,608 | B2 | * | 3/2003 | Pearson et al. ................. 548/182 |
| 7,442,720 | B2 | * | 10/2008 | Chan et al. ..................... 514/665 |
| 2002/0132795 | A1 | * | 9/2002 | Stogniew et al. .............. 514/114 |
| 2006/0232821 | A1 | | 10/2006 | Ranganathan |

OTHER PUBLICATIONS

Szwergold, "Alpha-Thiolamines such as cysteine and cysteamine act as effective transglycating agents due to formation of irreversible thiazoline derivatives", Medical Hypotheses, vol. 66, pp. 698-707 (2006).*
Lapolla et al., "Importance of measuring products of non-enzymatic glycation of proteins", Clinical Biochemistry, vol. 38, No. 2m pp. 103-115 (Feb. 2005).*
Ceriello A., "Hyperglycaemia:the bridge between non-enzymatic glycation and oxidative stress in the pathogenesis of diabetic complications", 1999 Diab Nutr Metab 12:42-46.
Hipkiss et al., "Pluripotent Protective Effects of Carnosine, a Naturally Occurring Dipetide", 1998 Ann. NY Acad. Sci. 854:37-53.
Hsu et al., "Five Cysteine-Containing Compounds Delay Diabetic Deterioration in Balb/cA Mice", 2004 J. Nutr 134 (12):3245-3249.
Keita et al., "Influence of penicillamine on the formation of early non-enzymatic glycation products of human serum proteins", 1992 Int. J. Clin. Pharmacol. Ther. Toxicol. 30:441-442.
Morgan et al., "Inactivation of cellular enzymes by carbonyls and protein-bound glycation/glycoxidation products", Archives of Biochemistry and Biophysics 2002 403:259-269.
Odetti et al., "Comparative Trial of N-Acetyl-Cysteine, Taurine, and Oxerutin on Skin and Kidney Damage in Long-Term Experimental Diabetes", 2003 Diabetes 52:499-505.
Ramamurthy et al., "Glutathione reverses early effects of glycation on myosin function", 2003 Am. J. Physiol. 285: C419-C424.
Szwergold et al., "Intrinsic toxicity of glucose, due to non-enzymatic glycation, is controlled in-vivo by deglycation systems including: FN3K-mediated deglycation of fructosamines and transglycation of aldosamines", 2005 Med Hypotheses 65:337-348.
Szwergold et al., "Carnosine and anserine act as effective transglycating agents in decomposition of aldose-derivced Schiff bases", 2005 Biochemical and Biophysical Research Communication 336:36-41.
Szwergold et al., "Nonenzymatic glycation/enzymatic deglycation:a novel hypothesis on the etiology of diabetic complications", International Congress Series 2002 1245:143-152.
Szwergold et al., "Transglycation—A Potential new Mechanism for Deglycation of Schiff's Bases", 2005 Ann. NY Acad. Sci. 1043:845-864.
van Boekel, M.A.M., "The role of glycation in aging and diabetes mellitus",1991 Mol. Biol. Rep. 15:57-64.
Wendt et al., "Glucose, Glycation, and RAGE:Implications for Amplification of Cellular Dysfunction in Diabetic Nephropathy", J. Am. Soc. Nephrol 2003 14:1385-1395.
Ziyadeh et al., "Effects of glycated albumin on mesangial cells:evidence for a role in diabetic nephropathy", 2003 Mol. Cell. Biochem. 125:19-25.

* cited by examiner

*Primary Examiner* — Kevin E Weddington
(74) *Attorney, Agent, or Firm* — Licata & Tyrrell P.C.

(57) ABSTRACT

The present invention relates to a method for inhibiting or reversing non-enzymatic glycation of the first intermediate of a biological moiety using an α-thiolamine. By inhibiting or reversing non-enzymatic glycation of the biological moiety, conditions such as aging and diabetic complications can be prevented or reversed.

2 Claims, No Drawings

METHOD FOR INHIBITING OR REVERSING NON-ENZYMATIC GLYCATION

This application claims the benefit of U.S. Provisional Application No. 60/806,661, filed Jul. 6, 2006, which is herein incorporated by reference in its entirety.

This invention was made in the course of research sponsored by the National Institutes of Health (NIDDK Grant No. R21DK062875-01). The U.S. government may have certain rights in this invention.

BACKGROUND OF THE INVENTION

Non-enzymatic glycation of macromolecules such as proteins and certain phospholipids (phosphatidylethanolamine and phosphatidylserine) appears to play an important role in the evolution of diabetic complications. With the discovery of fructosamine-3-kinase (FN3K) (Szwergold, et al. (1997) *Diabetes* 46:108A; Delpierre, et al. (2000) *Diabetes* 49:1627-34; Szwergold, et al. (2001) *Diabetes* 50:2139-47) and evidence that this kinase functions as a deglycating enzyme (Delpierre, et al. (2002) *Biochem. J.* 365:801-8; Delpierre, et al. (2004) *J. Biol. Chem.* 279:27613-20; Szwergold, et al. (2002) *Proceeding of the 7th International Symposium on Maillard Reaction*, vol. 1245C, Amsterdam/New York: Elsevier, p. 143-52) it is evident that, while the non-enzymatic glycation process is unavoidable (especially in homeothermic animals), it also appears to be counteracted in vivo by active deglycation mechanisms. Thus, the classical "nonenzymatic glycation" hypothesis of diabetic complications (Ceriello (1999) *Diab. Nutr. Met. Clin. Exp.* 12:42-6; van Boekel (1991) *Mol. Biol. Rep.* 15:57-64) has been modified to a "glycation/deglycation" hypothesis (Szwergold, et al. (2002) supra).

While data concerning the deglycating function of FN3K is accumulating, it is also becoming clear that FN3K alone cannot be the sole deglycating mechanism (Szwergold, et al. (2001) supra; Szwergold (2005a) *Med. Hypotheses* 65:337-48; Szwergold, et al. (2005b) *Ann. NY Acad. Sci.* 1043:845-64). It appears likely that FN3K-mediated deglycation of ketosamines is complemented by another process that lowers the concentration of aldosamines (A.K.A. Schiff bases) (Szwergold (2005a) supra; Szwergold, et al. (2005b) supra; Szwergold (2005c) *BBRC* 336:36-41). These data suggest that this FN3K-independent mechanism operates by the removal of the carbohydrate moiety from macromolecule-bound aldosamines by one or several of the numerous low molecular weight intracellular nucleophiles through a process of transglycation (Scheme 1).

SCHEME 1

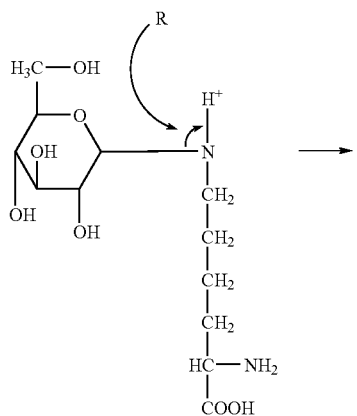

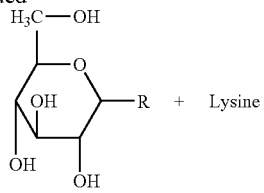

R = Nucleophile

It is not clear which nucleophiles are most relevant to transglycation in vivo. It has been suggested that, due to its ubiquity and high concentrations, glutathione may be the most important general transglycating agent (Szwergold (2005a) supra; Szwergold (2005b) supra) complemented in some tissues by peptides such as carnosine and anserine in the skeletal muscle (Szwergold (2005c) supra) and/or free amino acids, sulfhydryls and polyamines in other tissues (Szwergold 2005a).

SUMMARY OF THE INVENTION

The present invention is a method for inhibiting or reversing non-enzymatic glycation of a biological moiety by contacting the biological moiety with an α-thiolamine.

The present invention is also a method for preventing or reversing a condition associated with non-enzymatic glycation of biological moieties. This method involves administering to a subject in need of treatment an α-thiolamine so that non-enzymatic glycation of the first intermediate of biological moieties is inhibited or reversed thereby preventing or reversing the condition associated with non-enzymatic glycation in the subject.

DETAILED DESCRIPTION OF THE INVENTION

It is has now been found that α-thiolamines act as effective transglycating agents which function to break down the very first intermediate of non-enzymatic glycation by removing the glucose moiety from the intermediate. Advantageously, α-thiolamines are universally distributed and readily form irreversible thiazolidine products, such as glucose-cysteine, that appear to be exported out of cells and organisms (e.g., glucose-Cys is present in human urine). Accordingly, supplementation of human diet with one or more α-thiolamine compounds can lead to an inhibition of non-enzymatic glycation and its deleterious consequences, especially in diabetes.

Accordingly, the present invention is a method for inhibiting or reversing non-enzymatic glycation of the first intermediate of a biological moiety by contacting the biological moiety with an α-thiolamine. As used herein, the terms non-enzymatic glycation or non-enzymatic glycosylation are used interchangeably to refer to the Maillard reaction in which carbohydrates react with primary amines. The process of non-enzymatic glycation can, over time, lead to the formation of irreversible oxidized, aromatic and fluorescent ligands collectively referred to as the advanced glycation end-products (AGE's). Because early, as well as late, glycation products can impair the function of enzymes and structure proteins (Morgan, et al. (200) *Arch. Biochem. Biophys.* 403:259-69; Ziyadeh and Cohen (1993) *Mol. Cell. Biochem.* 125:19-25; Wendt, et al. (2003) *J. Am. Soc. Nephr.* 14:1382-95), it is important to inhibit glycation as early in the process as possible. While the analysis disclosed herein illustrates glycation via glucose, it is contemplated that glucose is only one of many glycating agents found in vivo which are involved in transglycation and formation of thiazolidines (Swamy, et al. (1993) *Exp. Eye Res.* 56:177-85; Szwergold, et al. (1995) *Biochem. Soc. Trans.* 25:150S; Thornalley (2002) *Int. Rev. Neurobiol.* 50:37-57; Slatter, et al. (2004) *J. Biol. Chem.* 279:61-9; Januszewski, et al. (2005) *J. Lipid Res.* 46:1440-9). As exemplified herein, the effectiveness of an α-thiolamine for inhibiting or reversing non-enzymatic glycation can be determined by NMR analysis or other conventional means for detecting glycation of biological moieties.

As used herein, inhibiting or reversing non-enzymatic glycation of the first intermediate of a biological moiety is intended to mean that the non-enzymatic glycation of a biological moiety susceptible to such glycation is prevented from occurring or, once it has occurred, is reversed by contacting the biological moiety with an α-thiolamine. This aspect of inhibiting or reversing non-enzymatic glycation of the first intermediate is novel in the art as conventional teachings indicate that while it is possible to inhibit the formation of advanced glycosylation end products, it would be nearly impossible to use agents which prevent the reaction of glucose with protein amino groups as agents that are capable of preventing initial glycosylation are likely to be highly toxic, and since the initial glycosylation comes to equilibrium in about three weeks, there is inadequate time available to achieve this objective (see, e.g., U.S. Pat. No. 5,334,617).

α-Thiolamines of use in accordance with the present invention include, but are not limited to, cysteine, cysteamine, N (2-mercaptoethyl)-1,3-propanediamine (WR-1065), N-acetyl-cysteine, penicillamine and derivatives and prodrugs thereof, e.g., prodrugs ribose-cysteine (RibCys) or ribosecysteamine (RibCyst). In particular embodiments, the α-thiolamine of the instant method is cysteine, cysteamine, or prodrugs thereof.

In accordance with the present invention, a biological moiety includes a cell, an enzyme, a structural protein, a signaling protein, a phospholipid, and any amine-containing biological macromolecule. By contacting the biological moiety with an α-thiolamine, non-enzymatic glycation of the first intermediate is inhibited or reversed.

The model of non-enzymatic glycation/active deglycation, including transglycation and FN3k-mediated deglycation, provides that the levels of both Schiff bases and ketosamines are controlled by deglycation thereby reducing the potential damage that can be caused by these early and transient glycation intermediates through enhanced production of oxygen free radicals (Hayashi, et al. (1977) *J. Agri. Food Chem.* 25:1282-7; Ortwerth, et al. (1998) *Biochem. Biophys. Res. Commun.* 245:161-5; Mullarkey, et al. (1990) *Biochem. Biophys. Res. Commun.* 173:932-9). However, to facilitate a decrease in the production of early glycation intermediates, supplementation of organs and organisms with transglycating nucleophiles such as α-thiolamines would protect against the adverse effects of hyperglycemia. Anti-hyperglycemic effects have been demonstrated for penicillamine (Keita, et al. (1992) *Int. J. Clin. Pharmacol. Ther. Toxicol.* 30:441-2), N-acetyl-cysteine (Hsu, et al. (2004) *J. Nutr.* 134:3245-9; Odetti, et al. (2003) *Diabetes* 52:499-505), glutathione (Ramamurthy, et al. (2003) *Am. J. Physiol.* 285:C419-24), and carnosine and anserine (Hipkiss, et al. (1998) *Ann. NY Acad. Sci.* 854:37-53).

Accordingly, the present methods and compositions are useful for arresting the aging of key proteins both in animals and plants, and concomitantly, conferring both economic and medical benefits as a result thereof. In the instance of foodstuffs, the administration of α-thiolamines holds the promise for retarding food spoilage thereby making foodstuffs of increased shelf-life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has been identified in the aging of key proteins by glycosylation and cross-linking. Thus, body proteins, and particularly structural body proteins such as collagen, elastin, lens proteins, nerve proteins and kidney glomerular basement membranes would all benefit in their longevity and operation by applying the method of the present invention. As such, by inhibiting or reversing the non-enzymatic glycation of the first intermediate of biological moieties, conditions associated with, resulting from, or as a consequence of non-enzymatic glycation can be prevented or reversed. Such conditions include, but are not limited to, retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present method is relevant to prevention of the noted conditions in patients either of advanced age or those suffering from one of the mentioned pathologies.

Wherein an α-thiolamine is utilized for in vivo or therapeutic purposes, the α-thiolamine is generally formulated in a pharmaceutical composition suitable for administration to a subject mammal or human. Pharmaceutical compositions can be prepared with a pharmaceutically effective quantity of one or more α-thiolamines of the present invention and can include a pharmaceutically acceptable carrier, selected from known materials utilized for this purpose. Such compositions can be prepared in a variety of forms, depending on the method of administration. For example, a liquid form would be utilized in the instance where administration is by intravenous or intraperitoneal injection, while, if appropriate, tablets, capsules, etc., can be prepared for oral administration. For application to the skin, a lotion or ointment can be formulated with the α-thiolamine in a suitable vehicle by including a carrier to aid in penetration into the skin. Other suitable forms for administration to other body tissues are also contemplated.

The invention is described in greater detail by the following non-limiting examples.

EXAMPLE 1

Materials

Glucose-cysteine, $^{15}N$ ethylamine and other common chemicals were purchased from Sigma, $^{13}C$-labeled glucose was obtained from Cambridge Isotopes and Omicron.

EXAMPLE 2

Glucose-Ethylamine

Glucose-ethylamine (G-E) was synthesized by incubating 2 M [1-$^{13}$C] glucose and [$^{15}$N] ethylamine for 3 hours at pH 12 and 37° C. At the end of the incubation period, about 75% of the starting material was converted to glucose-ethylamine existing in equilibrium with the starting materials.

EXAMPLE 3

Transglycation with Amines and Thiols

The reaction mixture (0.5 ml in a 5 mm NMR tube) included 250 mM HEPES, pH 8.5, 10% D$_2$O (for the purpose of locking the NMR magnetic field) and 50 mM concentration of a nucleophile of interest such as taurine. The reaction was performed at room temperature and it was initiated by adding an aliquot of G-E to a final concentration of 20 mM at which time consecutive $^1$H-decoupled, $^{13}$C NMR spectra of 20-minute duration were acquired using 580 scans, 60° pulses with NOE-decoupling and an interpulse delay of 2.065 seconds.

EXAMPLE 4

Transglycation with Thiolamines

The reaction mixture (0.5 ml in a 5 mm NMR tube) included 250 mM HEPES, pH 7.25, 10% D$_2$O (for the purpose of locking the NMR magnetic field) and 50 mM concentration of a compound of interest such as cysteine. The reaction was performed at room temperature and it was initiated by adding an aliquot of G-E to produce a final concentration of 20 mM at which time consecutive NMR spectra of 20-minute duration were acquired using 580 scans, 60° pulses and an interpulse delay of 2.065 seconds.

EXAMPLE 5

Synthesis of Thiazolidines

The various thiazolidine derivatives of thiolamines and glucose were synthesized by incubating 200 mM of the thiolamine with 10-60 mM glucose in 400 mM HEPES, pH 9.0, at 37° C. for 72 hours. At the end of the incubation period more than 95% of glucose was converted to the corresponding thiazolidine.

EXAMPLE 6

NMR

NMR spectra were obtained on the VARIAN UNITY-300 and -500 MHz machines. Spectra were analyzed using information from model compounds and chemical shift data known in the art (Neglia, et al. (1985) *J. Biol. Chem.* 260:5406-10; Mossine, et al. (1994) *Carbohyd. Res.* 262:257-70).

EXAMPLE 7

GC/MS

GC/MS analyses were preformed on a SHIMADZU G17A/5050 system. Samples were desiccated under a gentle stream of dry nitrogen or argon and converted to a trifluoroacetyl derivative by incubation in 100 µl of dry pyridine and an equal volume of MBTFA (Kishimoto, et al. (1997) *J. Chromatogr. B* 688:1-10). The injection volume was 1 µl and chromatographic separation was performed using a XT-5 column using the following program: 100° C. for 1 minute followed by a linear ramp from 100 to 220° C. at 40° C./minute, dwell for 2 minutes at 220° C. followed by another linear ramp from 220 to 270° C. at 40° C./minute and 5 minutes at 270° C. The injector temperature was set at 270° C. and the interface temperature was at 240° C.

EXAMPLE 8

Formation of Irreversible Thiazolidine Derivatives

Studies of reactions involving Schiff bases are intrinsically difficult as these compounds are labile at physiological pH. As such, to unambiguously follow Shiff base reactions in real-time, $^{13}$C NMR spectroscopy was employed. To utilize this technique efficiently, glucose-ethylamine (G-E) was synthesized and labeled with $^{13}$C at the C-1 position of the glucose moiety and with $^{15}$N at the amino group of the ethylamine as a model compound of glucosyl-lysine.

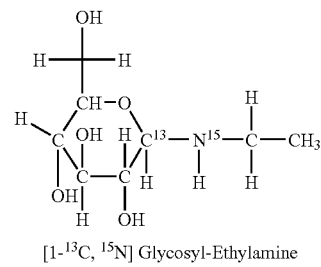

[1-$^{13}$C, $^{15}$N] Glycosyl-Ethylamine

Due to the spin-spin coupling between the nuclei of neighboring $^{15}$N and $^{13}$C atoms, the $^{13}$C-labeled C-1 peak of glucose appeared in the $^{13}$C NMR spectrum as a doublet resonating at 90.00 ppm. The unique signature doublet in the $^{13}$C NMR spectrum of G-E, its chemical shift as well as the distinct $^{13}$C chemical shifts of the other glucose-nucleophile adducts allowed for real-time observation reactions between G-E and various nucleophiles since cleavage of the ethylamine-glucose bond results in loss of the G-E doublet and the concomitant formation of new peaks corresponding to the new glucose-nucleophile adducts, e.g., the endproducts of transglycation of G-E, with glycine, taurine, spermidine and N-acetylcysteine. Because all of these transglycation products are labile at physiological pHs, the reactions were carried at a slightly alkaline pH of 8.5 to stabilize the reactants and products sufficiently so they could be followed by NMR over a span of several hours.

The only class of transglycation compounds that were stable at physiological pH were those resulting from reactions between G-E and α-thiolamines such as cysteine. This fact permitted transglycation reactions involving α-thiolamines to be performed at a physiological pH of 7.25. The most likely structures for such stable transglycation products were thiazolidines such as glucose-cysteine (G-Cys) that are known to form in reactions between aldehydes and thiolamines (Yao, et al. (1997) *Amino Acids* 12:33-40; Yao, et al. (1997) *Amino Acids* 12:85-94; Wrobel, et al. (1997) *Physiol. Chem. Phys. Med. NMR* 29:11-4).

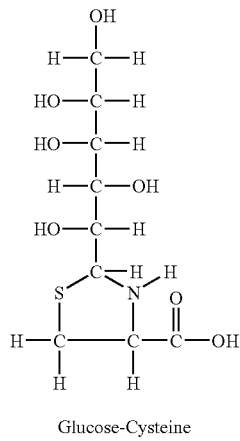

Glucose-Cysteine

To confirm that the product was indeed G-Cys, the $^{13}$C NMR spectra of authentic G-Cys was compared with those obtained by direct synthesis of cysteine and $^{13}$C-labeled glucose and the products obtained by a reaction of cysteine with G-E containing $^{13}$C-labeled D-glucose, labeled with at each one of the six carbons. The $^{13}$C NMR spectra of the products of all three reactions were identical, indicating that the product of transglycation between G-E and cysteine was indeed the thiazolidine, G-Cys. It is important to note that this reaction occurred only with glucose "activated" by its conjugation to ethylamine since incubation of glucose with cysteine under conditions identical to those used in the transglycation reactions (pH 7.25, 25° C. for 4 hours) did not result in formation of glucose-cysteine. The $^{13}$C NMR chemical shifts of the carbohydrate moiety of G-Cys are summarized in Table 1.

TABLE 1

| | C1 (ppm) | C2 (ppm) | C3 (ppm) | C4 (ppm) | C5 (ppm) | C6 (ppm) |
|---|---|---|---|---|---|---|
| β-Anomer | 71.17 | 75.02 | 72.30 | 72.285 | 71.97 | 63.84 |
| α-Anomer | 70.65 | 73.59 | 72.03 | 71.98 | 71.98 | 63.79 |

Results of similar incubation of other α-thiolamines with the [1-$^{13}$C] glucose/[$^{15}$N] labeled G-E with the corresponding chemical shits of the C1 carbon of the thiazolidine products are summarized in Table 2.

TABLE 2

| Glucose-Cysteine | | Glucose-Cys Gly | | Glucose-Cysteamine | | Glucose-Penicillamine | | |
|---|---|---|---|---|---|---|---|---|
| β (ppm) | α (ppm) | β (ppm) | α (ppm) | β (ppm) | α (ppm) | β (ppm) | β' (ppm) | α (ppm) |
| 71.17 | 70.65 | 71.10 | 70.51 | 71.83 | 71.37 | 68.1 | 67.81 | 66.00 |

The kinetics of decomposition of G-E and concurrent formation of thiazolidines indicate that while cysteine and cys-gly act as reasonably good transglycating agents, the decarboxylated derivatives of cysteine, cysteamine and penicillamine were much more potent, resulting in 80% and 70% conversion of G-E to glucosyl-cysteamine (G-Cytm) and glucosyl-penicillamine (G-Pen), respectively.

To detect and quantify thiazolidines and thiazolidine-like compounds in biological systems. GC/MS analyses of human urine and plasma from both normoglycemic and diabetic individuals were performed. Because of its commercial availability, the analysis focused on glucose-cysteine (G-Cys). A summary of the EI fragmentation data of G-Cys, is presented in Table 3.

TABLE 3

| Compound | Fragment (m/z) | | | |
|---|---|---|---|---|
| $^{12}$C-Glucose-Cysteine | 632 | 745 | 726 | 604 |
| $^{13}$C-Glucose-Cysteine | 638 | 751 | 732 | 610 |
| Fragment Intensity (percentage of total signal) % | 93.55 | 1.08 | 0.51 | 1.47 |

Ions listed in the first column in bold typeface are the major fragments used for quantitation.

Based on this data, selective ion monitoring (SIM) assays were performed on urine samples of five diabetic patients and two normoglycemic subjects. In this analysis, substantial amounts of G-Cys were detected in all samples examined, as evidenced by the presence of the characteristic ions at 632, 745, 604 and 726 m/z along with the C-13 ions of the internal standard at 638, 751, 610 and 732 m/z. The apparent amounts of G-Cys in urine of two normoglycemic individuals were 3.0 and 17 μmol/g creatinine, respectively, whereas in the five diabetic patients concentrations of G-Cys were significantly higher, ranging from 63 to 1750 μmol/g creatinine (average=565).

What is claimed is:

1. A method for inhibiting or reversing non-enzymatic glycation of the first intermediate of a biological moiety comprising contacting an enzyme, a structural protein, a signaling protein or a phospholipid with an α-thiolamine and measuring glycation of the enzyme, structural protein, signaling protein or phospholipid, wherein said α-thiolamine is selected from the group consisting of cysteamine, WR-1065, penicillamine, ribose-cysteine, and ribosecysteamine.

2. A method for reversing signs or symptoms associated with the onset of type II diabetes mellitus comprising administering to a subject in need of treatment an α-thiolamine and measuring glycation of the subject's enzymes, structural proteins, signaling proteins or phospholipids thereby reversing the signs or symptoms associated with the onset of type II diabetes mellitus in the subject, wherein said α-thiolamine is selected from the group consisting of cysteamine, WR-1065, penicillamine, ribose-cysteine, and ribosecysteamine.

* * * * *